United States Patent
Lee et al.

(10) Patent No.: US 8,534,285 B2
(45) Date of Patent: Sep. 17, 2013

(54) RESPIRATORY MASK

(75) Inventors: Gary C. J. Lee, I-Lan (TW); Hsuan-Liang Kang, Taipei (TW); Shu-Ping Zou, Taipei (TW)

(73) Assignee: Galemed Xiamen Co., Ltd., Fujian Province (CN)

( * ) Notice: Subject to any disclaimer, the term of this patent is extended or adjusted under 35 U.S.C. 154(b) by 702 days.

(21) Appl. No.: 12/768,346

(22) Filed: Apr. 27, 2010

(65) Prior Publication Data

US 2011/0146688 A1 Jun. 23, 2011

(30) Foreign Application Priority Data

Dec. 18, 2009 (CN) .......................... 2009 1 0261334

(51) Int. Cl.
*A61M 11/00* (2006.01)

(52) U.S. Cl.
USPC ................................. 128/206.25; 128/205.25

(58) Field of Classification Search
USPC ............ 128/206.25, 207.18, 205.25, 205.24, 128/206.24, 206.14, 206.21, 206.28, 200.24, 128/205.19
See application file for complete search history.

(56) References Cited

U.S. PATENT DOCUMENTS

| | | | | |
|---|---|---|---|---|
| 5,740,798 A * | 4/1998 | McKinney | ............... | 128/206.18 |
| 5,918,598 A | 7/1999 | Belfer et al. | | |
| 6,609,516 B2 * | 8/2003 | Hollander et al. | ........ | 128/201.17 |
| 6,769,432 B1 * | 8/2004 | Keifer | ....................... | 128/206.11 |
| 7,017,577 B2 * | 3/2006 | Matich | ..................... | 128/206.14 |
| 7,152,601 B2 * | 12/2006 | Barakat et al. | ........... | 128/206.14 |
| 8,020,700 B2 * | 9/2011 | Doshi et al. | ................... | 206/370 |
| 2002/0096178 A1* | 7/2002 | Ziaee | ........................ | 128/207.18 |
| 2010/0229872 A1* | 9/2010 | Ho | ........................... | 128/206.25 |

FOREIGN PATENT DOCUMENTS

CN 1501779 A 6/2004

* cited by examiner

*Primary Examiner* — Steven Douglas
(74) *Attorney, Agent, or Firm* — Greenberg Traurig, LLP

(57) ABSTRACT

A respiratory mask includes: a mask body for covering a part of a user's face; left and right wing portions, extending respectively from two opposite sides of the mask body and each having a rear surface adapted for attachment to the user's face; and an adhesive layer formed on the rear surfaces of the wing portions.

7 Claims, 4 Drawing Sheets

RESPIRATORY MASK

CROSS-REFERENCE TO RELATED APPLICATION

This application claims priority of Chinese application no. 200910261334.3, filed on Dec. 18, 2009.

BACKGROUND OF THE INVENTION

1. Field of the Invention

This invention relates to a respiratory mask.

2. Description of the Related Art

Referring to FIG. 1, a conventional respiratory mask 9 disclosed in Taiwanese utility model No. M346425 is shown to include a mask body 91 for covering a part of a user's face, a head strap 92 connected to the mask body 91 for fixing the mask body 91 at an appropriate position of the user's face, and a gas supply conduit 93 for supplying gas to the user.

Another respiratory mask for nose is disclosed in U.S. Pat. No. 6,581,602, and also includes head straps for fixing a mask body to the user's nose.

It is known that the conventional respiratory masks are usually fixed to the user by tying the head straps to the user's head.

SUMMARY OF THE INVENTION

Therefore, an object of the present invention is to provide a respiratory mask that is attached to a user's face via an adhesive layer.

Accordingly, a respiratory mask of the present invention comprises:

a mask body for covering a part of a user's face;

left and right wing portions, extending respectively from two opposite sides of the mask body and each having a rear surface adapted for attachment to the user's face; and an adhesive layer formed on the rear surfaces of the wing portions.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 1:
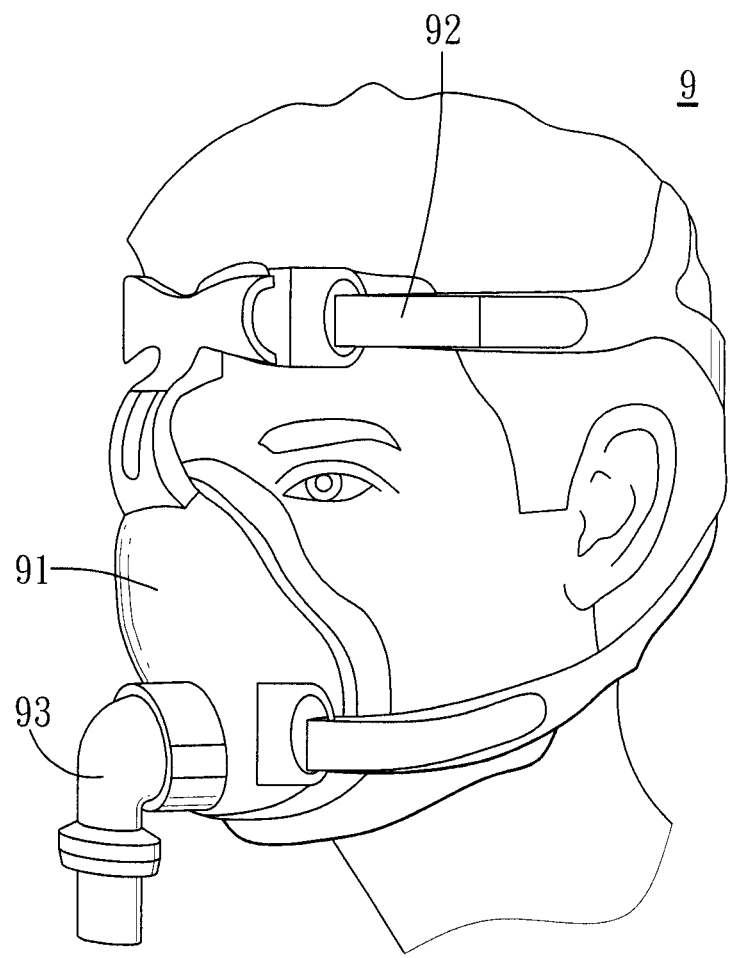
FIG. 1 shows a conventional respiratory mask disclosed in Taiwanese utility model No. M346425.
Figure 2:
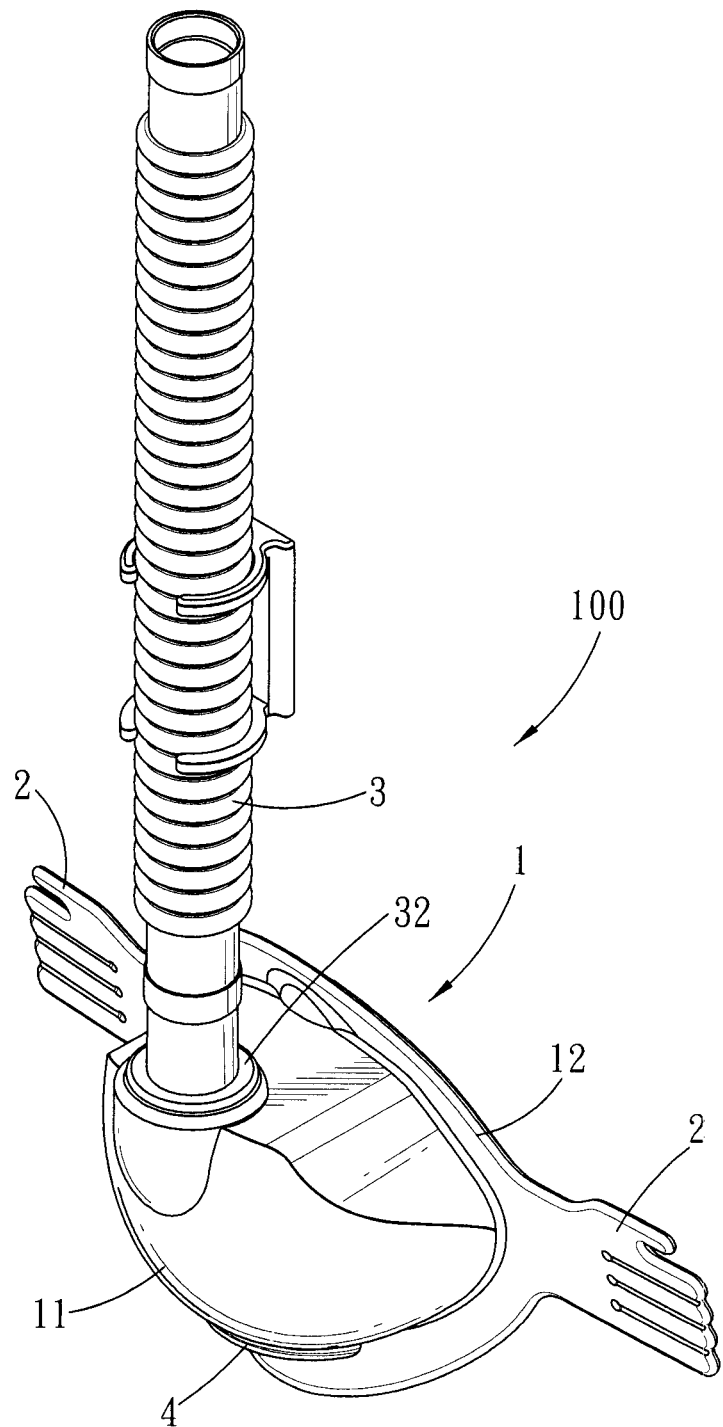
FIG. 2 is a perspective view of the preferred embodiment of a respiratory mask according to the present invention.
Figure 3:
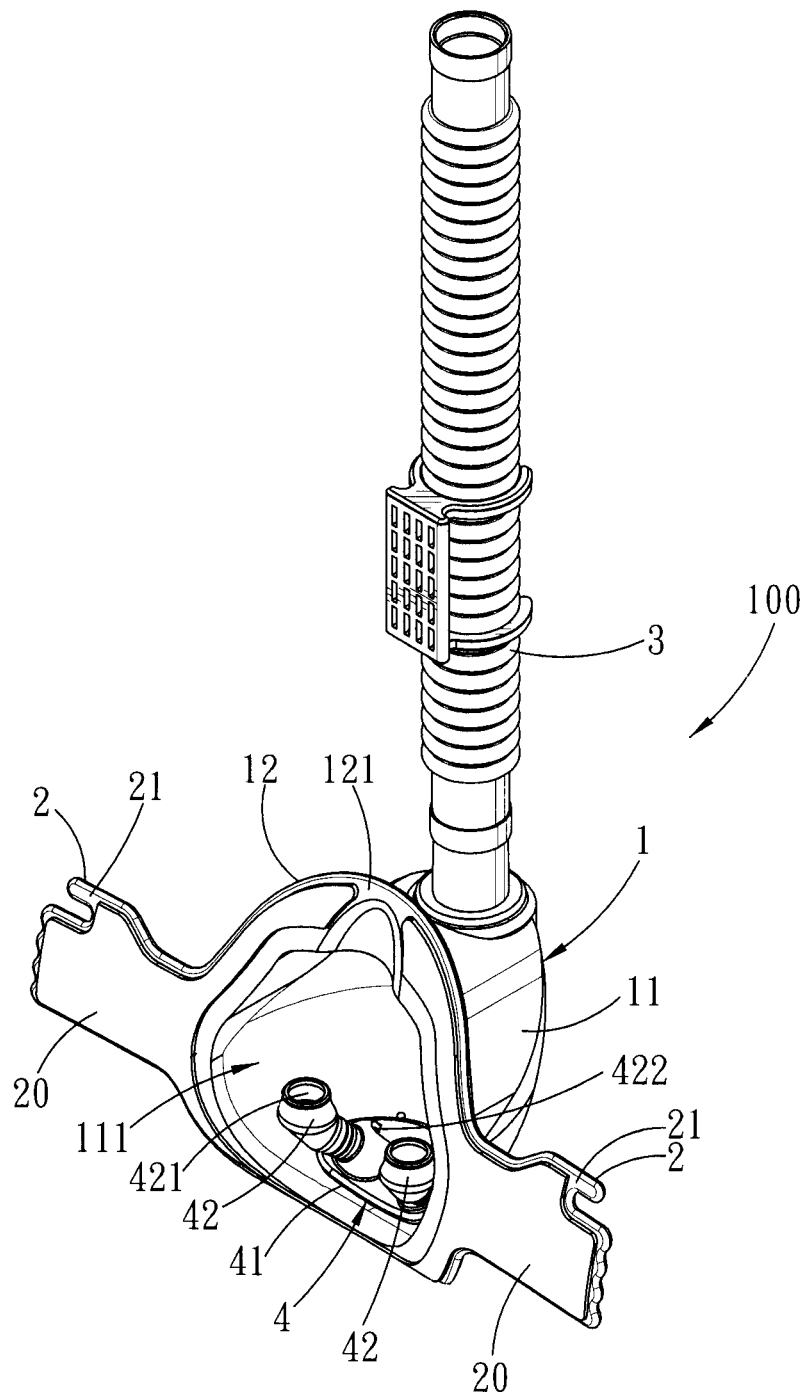
FIG. 3 is another perspective view of the respiratory mask of FIG. 2 viewed from a different angle.
Figure 4:
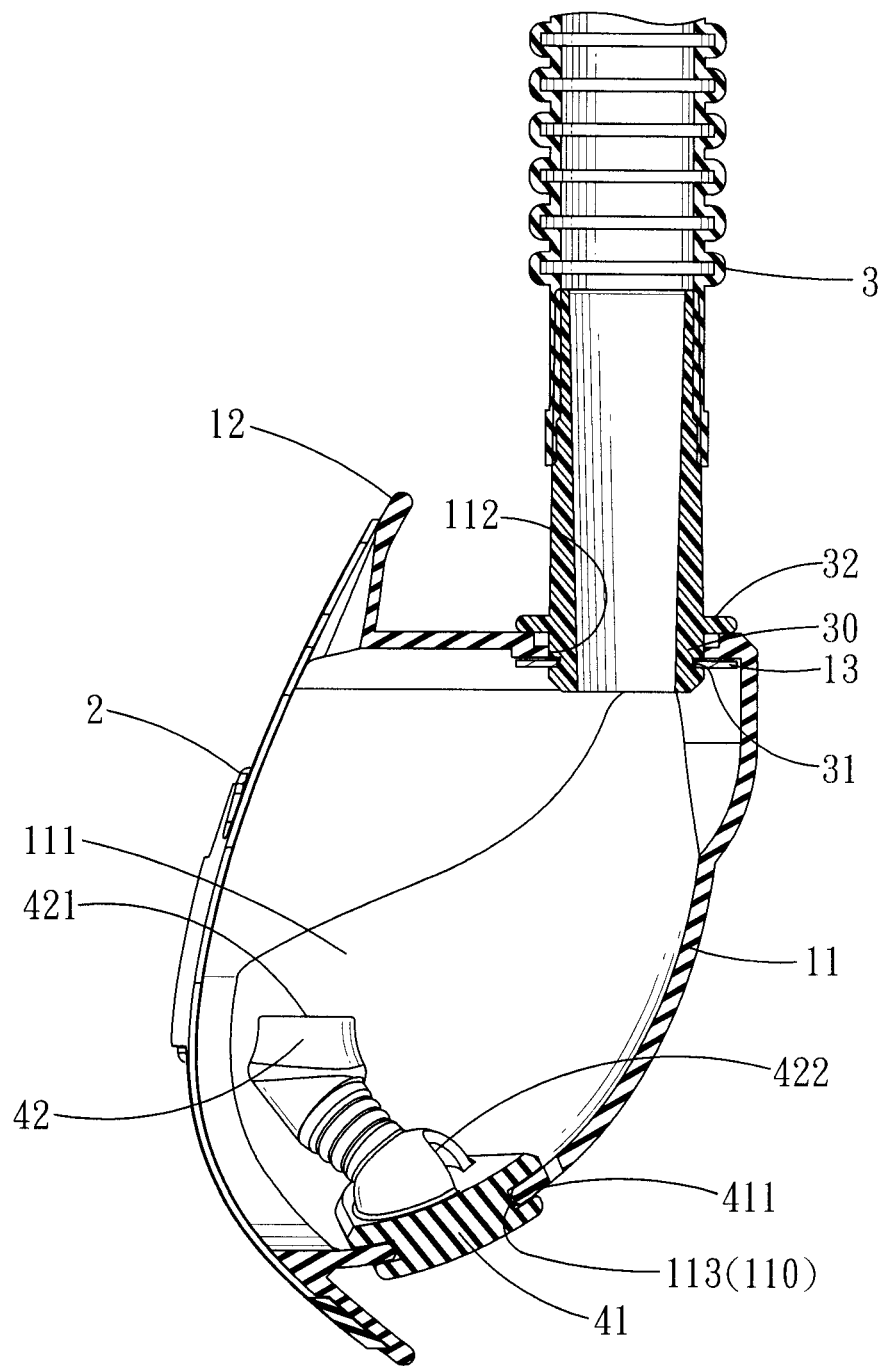
FIG. 4 is a cross-sectional view of FIG. 2.

Referring to FIGS. 2 to 4, a respiratory mask 100 according to the preferred embodiment of the present invention is shown to include a mask body 1, left and right wing portions 2, an adhesive layer 20, a gas supply conduit 3, and a tube seat 4. In the preferred embodiment, the respiratory mask 100 is used for covering a user's nose, but the present invention can also be in the form of a respiratory mask for covering the user's nose and mouth.

The mask body 1 for covering the user's nose includes a mask shell 11 and a peripheral flange portion 12. The mask shell 11 is substantially in a shape of a bowl, defines a recess space 111, and has a backward opening at a rear end of the mask shell 11. The peripheral flange portion 12 projects from the rear end of the mask shell 11 and extends around the backward opening to contact the user's face. The peripheral flange portion 12 has a rear surface 12, facing the user's face.

The left and right wing portions 2 extend respectively from two opposite sides of the mask body 1, and each of the wing portions 2 has a rear surface 21. In this embodiment, the wing portions 2 extend respectively from two opposite ends of the peripheral flange portion 12.

The adhesive layer 20 is made of an adhesive material that can maintain adhesive properties after washing (i.e., the adhesive layer 20 is water-washable). Preferably, the adhesive layer 20 is made of a pressure sensitive adhesive (PSA). The adhesive layer 20 is formed on the rear surfaces 21, 121 of the wing portions 2 and the peripheral flange portion 12. Thus, the rear surfaces 21, 121 of the wing portions 2 and the peripheral flange portion 12 are adapted for attachment to the user's face.

The mask body 1 and the wing portions 2 can be a one-piece structure made of silicone or other plastic, rubber, or elastomer.

When the mask body 1 covers the user's nose, the mask body 1 is fixed to the user's face by adhering the rear surfaces 21, 121 of the wing portions 2 and the peripheral flange portion 12 to the user's cheeks, instead of tying head straps to the user's head. Therefore, the respiratory mask 100 of the present invention is more convenient for wearing and can minimize discomfort caused to the user.

As best shown in FIG. 4, the mask shell 1 has a conduit hole 112 in an upper part of the mask shell 11. The conduit hole 112 is connected fluidly to the gas supply conduit 3 and is used for passing gas from the gas supply conduit 3 to the recess space 111. The gas supply conduit 3 has an insert end portion 30 that is inserted into the conduit hole 112.

In this embodiment, the gas supply conduit 3 has an annular groove 31, an annular flange 32 and a ring element 13, as best shown in FIG. 4. The annular groove 31 is formed on an outer surface of the insert end portion 30. The annular flange 32 projects from an outer surface of the gas supply conduit 3 proximate to an outer surface of the mask shell 11 so as to abut against the outer surface of the mask shell 11 around the conduit hole 112.

The ring element 13 is fitted in the annular groove 31. Since an inner diameter of the ring element 13 is smaller than an outer diameter of the gas supply conduit 3, and since an outer diameter of the ring element 13 is larger than a diameter of the conduit hole 112, the ring element 13 can abut against an inner surface of the mask shell 11 to prevent the insert end portion 30 from being released from the conduit hole 112 after the ring element 13 is fitted in the annular groove 31.

The annular flange 32 has an outer diameter larger than the diameter of the conduit hole 112, and thus, the annular flange 32 limits a downward movement of the gas supply conduit 3 when the annular flange 32 contacts the outer surface of the mask shell 11.

By using the annular groove 31, the annular flange 32 and the ring element 13, the insert end portion 30 of the gas supply conduit 3 is inserted rotatably into the conduit hole 112 relative to the mask shell 11. Thus, the user wearing the respiratory mask 100 can have an improved movability, especially when sleeping.

Furthermore, since the adhesive layer 20 is also formed on the rear surface 121 of the peripheral flange portion 12, when the left and right wing portions 2 are attached to the user's face, the peripheral flange portion 12 can also be adhered to the user's face around the user's nose. Accordingly, gas leakage from the respiratory mask 100 that can cause discomfort to the user's eyes can be avoided, especially when the respiratory mask 100 is used in combination with a continuous positive airway pressure (CPAP) system.

As shown in FIG. 4, the mask shell 1 further has a mounting hole 113 in a lower part of the mask shell 11. The mounting hole 113 is opposite to the conduit hole 112 and is confined by a looped edge 110 of the mask shell 11.

Referring to FIG. 3, the tube seat 4 includes a mounting plate 41 and a pair of nose tubes 42. The mounting plate 41 has a periphery formed with an annular groove 411 that receives and engages the looped edge 110 (see FIG. 4). The pair of nose tubes 42 are disposed in the recess space 111, and project upwardly and inclinedly from the lower part of the mask shell 11. Each of the nose tubes 42 includes upper and lower ends. The upper end of each nose tube 42 is formed with an outlet opening 421 adapted to be directed to the user's nose. The lower end of each nose tube 42 is connected to the mounting plate 41 and is formed with an inlet opening 422 communicated with the recess space 111.

Preferably, the recess space 111 of the mask shell 11 is gradually widened from the conduit hole 112 toward the nose tubes 42. Therefore, the gas from the conduit tube 3 can be guided toward the inlet openings 422 of the nose tubes 42.

Preferably, the mounting plate 41 is made of a flexible material, such as silicone or other rubber, to facilitate attachment of the mounting plate 41 to the mounting hole 113. As the mounting plate 41 is fixed to the mask shell 11 in a detachable fashion, the nose tubes 42 are replaceable. As such, the respiratory mask 100 can be provided with differently sized nose tubes 42 to suit different users.

In addition, the respiratory mask 100 can be used as a face mask or a nose mask in a dental operation to supply an anaesthetic to the user's nose via the gas supply conduit 3.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

What is claimed is:

1. A respiratory mask, comprising:
    a mask body for covering a part of a user's face, said mask body including: a mask shell which defines a recess space and which has a backward opening at a rear end of said mask shell; a peripheral flange portion which projects from said rear end of said mask shell and which extends around said backward opening to contact the user's face; and a conduit hole; left and right wing portions, extending respectively from two opposite ends of said peripheral flange portion and each having a rear surface adapted for attachment to the user's face;
    a gas supply conduit connected fluidly to said conduit hole;
    a pair of nose tubes which are disposed in said recess space, and which project upwardly and inclinedly from a lower part of said mask shell within said recess space, each of said nose tubes including an inlet opening communicated with said recess space and an outlet opening adapted to be directed to a nose of the user;
    a mounting plate disposed at said lower part of said mask shell and opposite to said conduit hole, each of said nose tubes having a lower end connected to said mounting plate and formed with said inlet opening and further having an upper end formed with said outlet opening; and
    an adhesive layer formed on said rear surfaces of said wing portions.

2. The respiratory mask of claim 1, wherein said peripheral flange portion has a rear surface facing the user's face, said adhesive layer being further formed on said rear surface of said peripheral flange portion.

3. The respirator mask of claim 1, wherein said mask shell further has a mounting hole disposed in said lower part of said mask shell, said mounting plate being detachably fitted in said mounting hole.

4. The respiratory mask of claim 1, wherein said recess space of said mask shell is gradually widened from said conduit hole toward said nose tubes.

5. The respiratory mask of claim 3, wherein said mounting hole is confined by a looped edge of said mask shell, and said mounting plate is made of a flexible material and has a periphery formed with an annular groove that receives and engages said looped edge.

6. The respiratory mask of claim 1, wherein said gas supply conduit has an insert end portion that is inserted rotatably into said conduit hole, and an annular flange projecting from an outer surface of said gas supply conduit to abut against an outer surface of said mask shell around said conduit hole, said insert end portion having an annular groove formed on an outer surface of said insert end portion, and a ring element fitted in said annular groove to abut against an inner surface of said mask shell, thereby preventing said insert end portion from being released from said conduit hole.

7. The respiratory mask of claim 1, wherein said adhesive layer is a water-washable pressure sensitive adhesive.

\* \* \* \* \*